United States Patent [19]

Le Roy

[11] 4,003,141

[45] Jan. 18, 1977

[54] INTRACRANIAL PRESSURE MONITORING DEVICE

[75] Inventor: Pierre L. Le Roy, Wilmington, Del.

[73] Assignee: New Research and Development Lab., Inc., Wilmington, Del.

[22] Filed: Apr. 1, 1975

[21] Appl. No.: 564,039

[52] U.S. Cl. .............................. 35/17; 128/2.05 E
[51] Int. Cl.² ........................................ G09B 23/32
[58] Field of Search ................. 128/2.05 E, 2.05 D, 128/2 P, 2.1 A, 350 V; 73/388 R, 389, 391, 4 R; 35/17

[56] References Cited
UNITED STATES PATENTS

| 3,686,958 | 8/1972 | Porter | 128/2.05 D |
| 3,802,096 | 4/1974 | Matern | 35/17 |
| 3,877,137 | 4/1975 | Hakim | 128/2.05 E |

*Primary Examiner*—Anton O. Oechsle
*Assistant Examiner*—Arnold W. Kramer
*Attorney, Agent, or Firm*—Connolly and Hutz

[57] ABSTRACT

An intracranial pressure monitoring device such as for monitoring pressure in the skull of a living human or in a simulated skull includes a pressure sensor which is mounted in the skull at the situs where the pressure is to be monitored and pressure transmitting means for transmitting a value representative of that pressure to indicating means externally of the skull.

16 Claims, 7 Drawing Figures

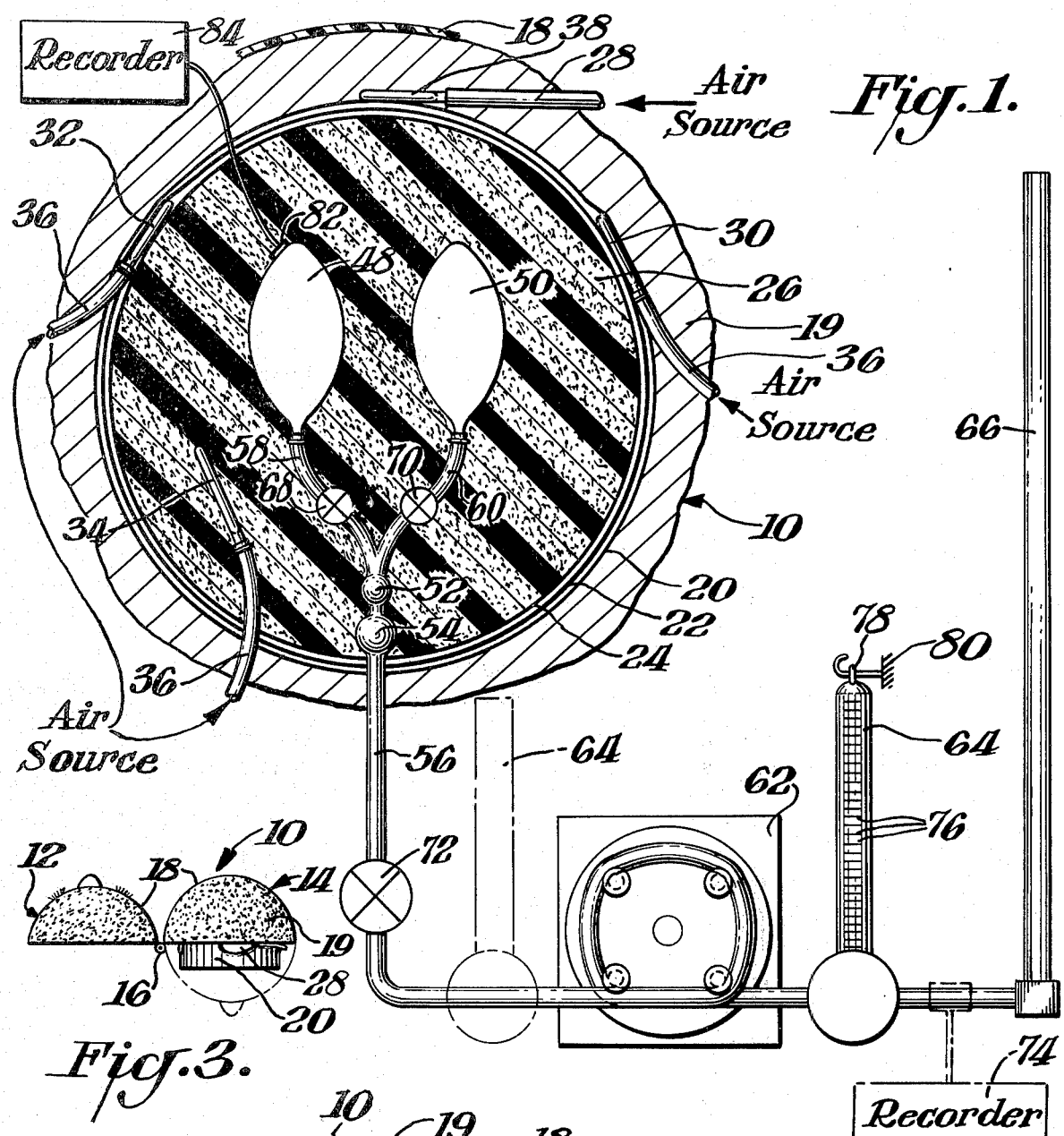

INTRACRANIAL PRESSURE MONITORING DEVICE

BACKGROUND OF THE INVENTION

There is a complex interrelationship between intracranial pressure and such physiological parameters as respiratory rate and rhythm and pulse. Where abnormal intracranial pressure exists it would be desirable if a system could be provided in connection with the treatment of such pressure as, for example, by drugs or mechanical relief to determine when the proper or normal pressure has been reached. Along the same lines it would also be useful if a bench model simulating a human skull could be provided to serve the multiple purposes of being an aid in diagnostic, therapeutic, experimental and educational exercises. If such a model were provided which simulates the changes in intracranial pressure and the aforementioned physiological parameters, the model could achieve the wide range of applications noted above. For example, the model could function as a diagnostic aid to test monitoring systems adapted transdurally or intraventricularly, for selectively determining from a wide range of intracranial pathologies abnormalities whose clinical signs may appear the same as other neurological dysfunctions. With such a model an accurate differential diagnosis would be facilitated.

Such a bench model would also have therapeutic application. In this respect such a model could be incorporated in a bio-feedback system or servomechanism which administers osmotic cerebral decompressants on a demand basis or regulates the flow through valve shunts.

Such a model would also have experimental application and would be useful in research and development of diagnostic and therapeutic control systems as described above. The model would permit testing the efficacy of both conventional and new drugs and mechanical shunts. The principles of the model could also be utilized in direct human application in connection with the use of drugs and mechanical shunts.

Such a model would also have an educational application for use in teaching the neurophysiology of disorders related to pressure changes to both student and clinical staff. Accordingly, complex situations could be demonstrated in a simplified manner.

There has been increasing emphasis placed on the methods of monitoring disorders of the central system and intracranial states. Accordingly, it is vital to instruct health care personnel in the recognition of the various combinations of life threatening neurological conditions which are produced by trauma, stroke, neoplasm or congential disorders.

SUMMARY OF THE INVENTION

An object of this invention is to provide an intracranial pressure monitoring device capable of both human and bench model application to fulfill the needs described above.

A further object of this invention is to provide such a device in connection with a teaching model which in turn provides a concise and clear method of presenting a substantial amount of information and allows for an observation and understanding of the intracranial changes that are happening.

A still further object of this invention is to provide such a device which is capable of demonstrating the importance of pressure monitoring systems, since the conditions producing the numerous abnormalities manifest themselves with very similar, if not identical, clinical signs and the signs do not appear until brain damage has occurred.

In accordance with this invention an intracranial pressure monitoring device includes a pressure sensor which is mounted within a skull of the body at the situs where the pressure is to be monitored. Situs pressure transmitting means is arranged for transmitting a value representative of that pressure to indicating means disposed externally of the body. The device may be used in direct human application by mounting the sensor, in the form of a tambour, in the human skull and the transmitting means may be electronic means for transmitting electrical impulses to the indicating means.

In an alternative form of this invention the device may be mounted in a bench model which simulates the human skull. In such device the situs may, for example, be a simulated ventricle. Abnormal pressure creating means may be provided at the simulated skull remote from the simulated ventricle to create an abnormal condition which is transmitted to the ventricle by a yieldable mass, such as by urethane, and the change in pressure to the ventricle may be transmitted through tubing externally of the simulated skull to a suitable indicating device such as a manometer or a conventional recorder.

THE DRAWINGS

FIG. 1 is a cross-sectional view in elevation of an intracranial monitoring device incorporated in a bench model;

FIG. 2 is an exploded view of the bench model illustrated in FIG. 1;

FIG. 3 is a plan view of the bench model illustrated in FIG. 2;

FIG. 4 is a schematic view representing possible sites for use with the monitoring device;

DETAILED DESCRIPTION

Figure 5:
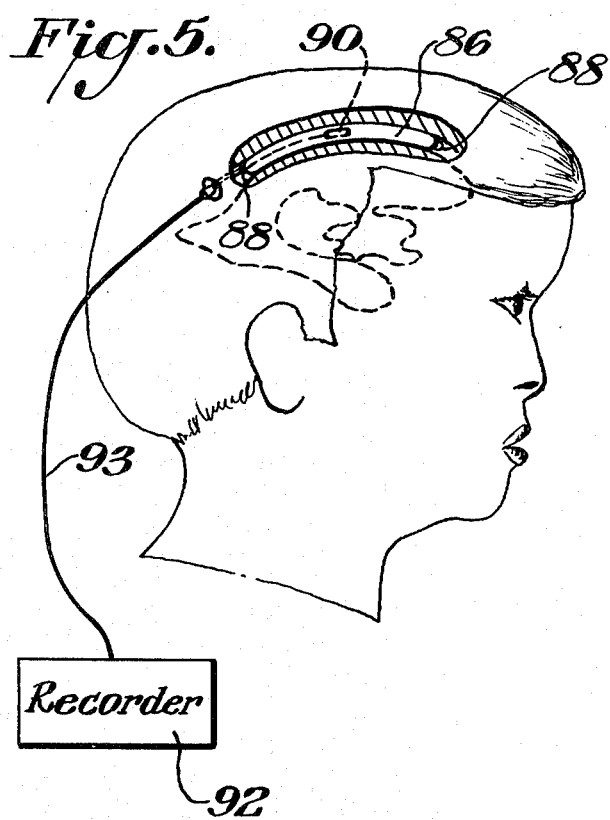
FIG. 5 is a schematic view showing the device of this invention in human application.

In accordance with this invention, whether for human application or as a bench model, the intracranial pressure monitoring device includes a pressure sensor which is mounted within the skull of a body at the situs where the pressure is to be monitored and situs pressure transmitting means transmit a value representative of the pressure to indicating means disposed externally of the body. The body itself is subject to physiological parameters and the monitoring device is intended to demonstrate, by means of the pressure indicating means what pressure actually exists at the situs so that a determination can be made if this pressure is abnormal. For example, in human application such physiological events are respiratory rate and rhythm and pulse inherently exist. Where a bench model is used such events are artificially created. In human application the pressure sensor is preferably a tambour which is mounted at the desired situs and the pressure transmitting means may be electrical pulses transmitted by a transducer mounted within the tambour or may be from flow communication within the tambour to a suitable indicating device which could be either a sophisticated instrument or a more simple manometer. For the bench model a tambour may also be used in a manner similar to that previously described with respect to human application. Alternatively, the pressure may be transmitted from the situs by means of tubing connected at the situs and leading externally of the model to a suitable pressure indicator.

FIGS. 1–3 illustrates a bench model incorporating the concepts of this invention. As illustrated therein, the device includes a model 10 of a human skull which is formed in two halves simulating the front 12 and back 14 of a human with the halves being hinged together as indicated by the reference numeral 16 to provide accessibility therein. The hinging permits the halve sections of the skull to open 180°. The outer layer 18 of the skull model 10 is made of a suitable plastic material which is firm and non-yielding such as one of the various types of acrylics. Since the model is intended to function as a demonstration device, in the preferred form of the invention the material selected is translucent or transparent whereby any dynamic action within the skull would be visible to the viewer. As illustrated in FIG. 3, for example, a latex caulking 19 is provided on the inner surface of the model but the face portion thereof is left uncaulked so that simulated parts such as ventricles may be visible through the face. The caulking adds sufficient stiffness in combination with the plastic outer layer 18 to function or accurately simulate the corresponding portion of the human skull.

Mounted beneath the outer shell formed by layer 18 and caulking 19 are simulated membranes 20, 22, 24. The simulated membranes are, for example, plastic sheets, such as polyethylene, which are disposed inwardly of the hard outer shell and are mounted around a yieldable mass of transmitting material 26, such as urethane sponge material. Mass 26 reacts in the same manner as a human brain in that the application of pressure thereto causes a combined compressive and lateral shifting action toward the interior of the skull because of resistance from the hard shell. This action is advantageously used to transmit to the skull interior pressure applied thereto. The provision of mass 26 thereby imparts dynamic characteristics to the device. Simulated members 20, 22, 24 correspond to the dura, arachnoid and pia membranes, while sponge or mass 26 functions as the brain. Although three individual membranes 20, 22, 24 are illustrated, in its broad aspect the invention may be utilized with a single membrane which functions as three membranes. Individual membranes 20, 22, 24, however, more accurately reflect the different functions of the membranes. Thus, for example, membrane 24 simulates the pia which is a structural membrane upon which the very delicate blood vessels grow on the brain and are suspended. Membrane 22 simulates the arachnoid which is a waterproof covering structure which contains within the pia and the arachnoid compartment the spinal fluid compartment itself. Between the arachnoid 22 and the dura 20 is a subdural space which is only a potential space and only opens up with fluid communication in disease and which in the model can be simulated. Abnormal pressure conditions at each of these membranes represent such occurrences as traumatic from a head injury, hemorrhaging, stroke, aneurysm, etc.

Simulated abnormal pressure conditions are created in accordance with this invention at various locations within the model 10. For example, adjacent each membrane to the outside thereof an abnormal pressure creating means is arranged. Specifically, abnormal pressure creating means 28 is provided adjacent the simulated dura membrane 20, abnormal pressure creating means 30 is provided to the outside of and adjacent membrane 22 and abnormal pressure creating means 32 is provided to the outside of and adjacent simulated pia membrane 24. Any other abnormal pressure creating means may be provided in any suitable locations such as indicated by pressure creating means 34 mounted within the simulated brain 26. Each of these abnormal pressure creating means is in the form of a tube 36 connected to an air source and provided with a closed inflatable member 38 at its end thereof. Accordingly, the supply of air or other suitable fluid through tube 36 creates a pressure in member 38 which acts against its environment such as a respective membrane. The sponge material or yieldable mass 26 responds to this creation of abnormal pressure by being compressed and shifting laterally thus transmitting the abnormal pressure inwardly in the same manner that the brain would react in response to an abnormal pressure being created in a human.

As indicated in FIG. 4, the abnormal pressure may be detected at various suitable locations. For example, reference numeral 40 represents the ventricles which would reflect conditions such as of a congential type as hydrocephalus. Reference numeral 42 represents a subdural situs indicative of traumatic or subdural hematoma. Reference numeral 44 represents abnormal conditions such as inflammatory, brain abcess, neoplastic or brain tumor. Reference numeral 46 represents degenerative ailments such as brain atrophy.

Referring again to FIG. 1 in the model 10 illustrated therein, the sites being monitored are the various ventricles or more specifically the simulated first ventricle 48 and the simulated second ventricle 50. The third and fourth ventricles 52, 54 are also schematically represented and may likewise be monitored by suitable application of the invention. In practice the simulated ventricles are in the form of inflatable sacs analogous to balloons. As later described, an internal pressure is created in the sacs representative of the physiological parameters such as simulated pulse and respiration. Because of the pressure transmitting ability of sponge material 26, however, the abnormal pressure created at, for example, one or more of the membranes is transmitted to the simulated ventricle to cause a pressure thereagainst and such abnormal pressure acting upon the ventricle would be monitored by the invention.

The simulated pulse and respiratory conditions are applied to the ventricles 48, 50 by means of a tubing 56 having a separate branch 58, 60 for each of the ventricles. Tubing 56 is mounted to a commercially available pump 62 which acts upon the fluid in the tubing to simulate the physiological parameters of pulsive and respiratory rate and rhythm. Such a pump for example may be the commercially available Holter H series 900 pump. The purpose of pump 62 is to add a pulsating characteristic to the fluid in tube 56 and the ventricles to simulate a pulse wave such as occurring between 50 to 150 pulses per minute thus simulating heart beat that changes with intracranial pressures. The fluctuation should be in the neighborhood of several millimeters of water changes when a manometer 64 is used as the indicating device. In other words from 0 to 5 millimeters of water would be in the change in the manometer level as simulated in the body. The second pulsator characteristic of the pump is that of respiration in a variable rate ranging between 0–50 and a third pulsator characteristic is that of intracranial pressures itself which may be a long duration pulse lasting several minutes to hours or perhaps even days. In model 10 for purposes of economy only a single pump 62 is used which has three variable pulsator characteristics, although it is not precisely accurate as to what happens in the body since in using one pump it is sequentially related, whereas in the actual body the pulse, respirations and intracranial pressure changes are not necessarily synchronous. Accordingly, where greater accuracy is desired, at the expense of economy, the device could include three separate pump systems used to make the variables very precise.

In the system illustrated in FIG. 1 a reservoir 66 is arranged to provide a source of fluid such as water to the flexible tubing 56. Reservoir 66 may be a U-shaped tube to permit variation in the "normal" condition. The liquid source also functions as a simulated drain to the spinal column. The manometer 64 is in fluid communication with the tubing 56 and the amount of liquid flowing through the tubing is reflected at a calibrated level in the manometer. This level represents the normal or comparison value. Changes of pressure in tubing 56 resulting from the creating of pressure at the ventricles would likewise provide a visual indication of the affect that the abnormal pressure has on the ventricle. Tubing 56 is illustrated as being in fluid communication with both ventricles 48, 50 through branches 58, 60. Suitable valves 68, 70, however, are provided in the event it is desired to reflect the affects on only a single of the ventricles. Central shut off valve 72 is also provided in tubing 56 for general control purposes. FIG. 2 illustrates an arrangement where such valves could be external of mass 26.

Although manometer 64 is illustrated as being between pump 62 and liquid source 66, the manometer may be in any other suitable location such as indicated in phantom in FIG. 1. Additionally, a more sophisticated indicating means may be provided instead of or in addition to manometer 64, the indicating means being illustrated in phantom as recorder 74. In such case the manometer would function as a check reading for the recorder. Suitable recorders are commercially available and such a recorder may be, for example, the Tektronix Model 412. Where a manometer is used, in accordance with an ancillary feature of this invention, the manometer is made in tube form of a flexible material having level indicating calibrations 76 thereon with the flexible tube having a loop, hook or other means 78 and its upper end to be mounted suspended from a fixed surface 80. The advantage of such a flexible manometer is that it can be stored easily during non-use requiring less space.

As previously indicated, the face portion 82 of model 10 is transparent and allows for a cut-away view of the brain. Thus ventricles 48, 50 are readily visible. In other words there is no sponge material 26 provided in front of the ventricles so that the model can be seen with the face portion closed or can be opened by hinge 16 for further demonstration purposes. The invention may of course be practiced with sponge material 26 completely surrounding the ventricles and with face portion 82 opaque. The model may include the further physiological feature of the cerebral aneurysm which would be a balloon system disposed at the base of yieldable mass or sponge 26.

As should be apparent from the above description, in use fluid is supplied to tubing 56 from source 66 and pumped into ventricles 48, 50 by means of pump 62 which simulates the various physiological parameters. The intracranial pressure with respect to ventricles 48, 50 is visible to the user by means of manometer 64 and/or recorder 74. An abnormal pressure is then created by directing air through tubing 36 into its inflatable receptacle 38. The flow of air may be constant from a pump or from a syringe. The abnormal pressure created thereby is transmitted to ventricle by means of the yieldable mass or sponge material 26 which in turn creates a pressure change against ventricles 48, 50 and this pressure change is then reflected by a changes in the level in manometer 64 or the reading or graph produced by recorder 74. In other words the application of pressure from mass 26 to flexible ventricles forces the fluid in tubing 56 to back up thereby causing a change in level, for example, in manometer 64.

In place of the manometer 64 and/or recorder 74 the intracranial pressure may be detected by provoiding a conventional tambour 82 disposed at the desired situs such as ventricle 48. The tambour may, for example, include a transducer which sends electrical pulses to a suitable recorder 84 to reflect the intracranial pressure with respect to ventricle 48. A suitable recorder 84 may be for example commercially available Sanborn 360 similar to an EKG machine employing Stalham transducers, Trantec or Bell & Howell which are commercially available and interchangeable.

As later described the tambour system can be applied in model 10 or used independently as its own sensor as an implant in humans. Such tambours are known in the art and its features include a medical grade silicone which is radio-opaque constructed in such a way that it will withhold either fluid (i.e. physiologic saline) and/or other solutions such as colloids or gases such as air or nitrogen. Tambour 82 would be mounted beneath that structural layer that simulates the inside of the intracranial cavity and external to the pulsatile part. When applied in humans the tambour would be placed either outside or inside the dural membranes of the body or would be implanted within the brain substance itself within the human as later described. The inward pressures against the tambour act in a positive manner to coaptate it against the outside of the fixed skull model or in a human in the skull itself as a mounting technique. Accordingly, the tambour may be used in the model, in animal investigation work as an implant system or in human medical applications in regards to both diagnosis and treatment. The tambour may be a single tambour fluid filled and may be attached to a manometer and also a priming fluid. The tambour may be attached to an electronic recorder such as the previously noted Textronics 412 or through the use of transducers to a Sanborn recorder similar to the electrocardiograph principle. Multiple tambours may be employed either in pairs or in sets of four or six attached either singly or in parallel series so that it will sense the pressure difference recorded in tambour No. 1 in a system or tambour No. 3, so that single or overall pressure changes can be detected and recorded. This permits application over a global distribution, that is over the entire surface of the top of the brain, along the side of the brain and simultaneously on the under surface of the brain as deemed necessary. The tambour may take any suitable shape and may be of, for example, circular form having a diameter of from 2 to 4 cm. Alternatively, the tambour may be ellipitically shaped or rectangularly shaped varying from 2 by 6 cm to 4 by 10 cm to give a larger surface area for noting pressure changes. When fluid is inserted into the tambour systems the fluid would be biologically inert and sterile. When used on animals or on the model the fluid could contain visual dyes to demonstrate changes in diameter of the sensor.

Figure 6:
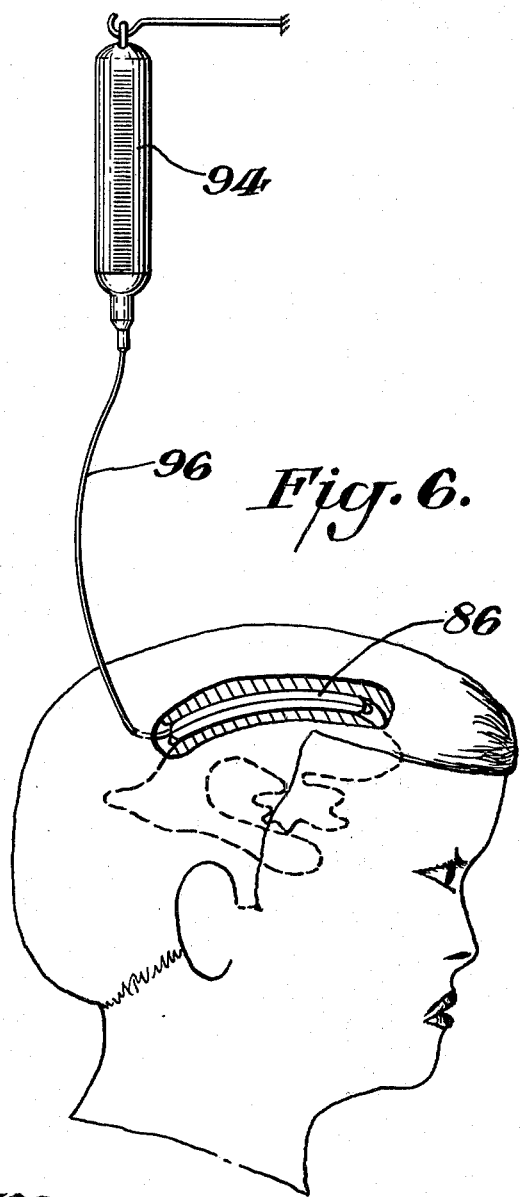
FIG. 6 is a schematic view similar to FIG. 5 of an alternative form of this invention.

FIGS. 5-6 show a novel form of tambour 86 which is designed particularly for use in this invention. As indicated therein, the tambour 86 is of elongated form made from a flexible material and is provided with a pair of loops 88 at each end thereof. This particular form of tambour is intended to cooperate with a known inserting tool referred to in the art as a Gigli saw guide which is a flat metal band having a hook at each end onto which loops 88 may be inserted. Such an inserting tool is particularly advantageous since it can bend and thus conform in shape to its particular environment. After the tambour has been inserted in its desired location the inserting tool is manipulated in a conventional manner to detach loops 88 from the tool so that the tool can be withdrawn and the tambour mounted in place. As illustrated in FIG. 5, tambour 86 includes a transducer 90 which sends electrical pulses through conductor 93 to recorder 92 such as a Sanborn 360 model. FIG. 6 illustrates the alternative where tambour 86 is in fluid communication with flexible manometer 94 of the type previously described through tubing 96.

For use of the monitoring device in human application such as illustrated in FIG. 5, the surgeon makes a hole in the cranium by standard operating techniques, either over the front of the cranium, off to one side as a single hole, or multiple holes, over the top and underneath the section of the skull (i.e. over the cerebellum.) The sensor which may be a tambour is then introduced through the cranial opening similar to a hole in ice underneath to the dura and outside the dura, so that the sensor is then coaptated between the inner surface of the skull and the outside of the dura if that should be the situs to be monitored or inside the dura or inside the brain itself as desired. The tube 96 is then run out from the skin of the scalp, fluid filled, and attached to a system of a manometer 94 or recorder 92 as previously described. After closure the patient is returned to a hospital unit where the monitors are turned on. The system is calibrated with the use of an open air manometer and recording is begun either on a single or continuous basis. During such human application the pressure monitoring device may be used in cooperating with the treatment of the abnormal pressure condition such as by drugs or mechanical relief (e.g. a tap shunt) and the application of the treatment may be terminated when the correct pressure information is monitored. By the activation of automated pumps, for example, durg therapy can be increased as the intracranial fluid fluctuates. When the human condition is terminated the sensor would be removed from the patient.

An additional use of the invention is that it permits the testing of mechanical appliances, such as shunts, under a variety of simulated abnormal pressure conditions or under in-vitro use.

Figure 7:
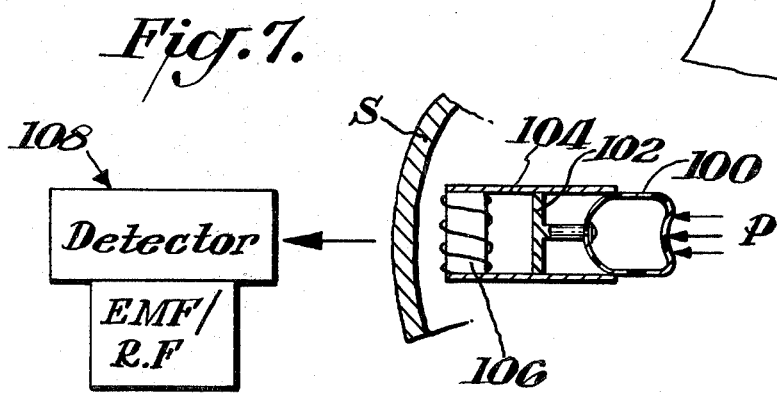
FIG. 7 is a fragmentary view in cross-section schematically illustrating yet another form of this invention.

FIG. 7 illustrates yet another form possible for carrying out this invention. As indicated therein a tambour 100 of any suitable type such as previously described is mounted within the skull S and expands or contracts in accordance with the pressure sensed at that site. Attached to the tambour is a metallic slide member 102 mounted, for example, in housing 104 at the end which is mounted a magnet 106 for generating a suitable magnetic field. Magnet 106 may, for example, by an electro-magnet. A suitable electro-magnetic force sensor 108 detects the change in the electro-magnetic force field in accordance with the change in relative position between slide member 102 and magnet 106. The amount of change of the magnetic force field can be calibrated to correlate to the change in pressure as detected by the tambour. Accordingly, with this arrangement it is possible to provide a means of sensing the pressure changes externally of the body without the external attachments such as wires, tubes, etc., which would be used with prior embodiments. This arrangement frees the patient for movement and allows a complete freedom of mobility from any otherwise attached recording system. The system is suitable for implantation in various sites such as cranial, spinal, joint, etc., and may be used in various biological systems such as human and animal as well as bench model.

Although this invention has been particularly described with respect to abnormal conditions in the brain, the concepts of this invention may be practiced in other manners wherein dynamic conditions occurring in the body are monitored. For example, a heart or lung might be simulated in a situation that would affect the brain system and its affects similarly monitored. Additionally, model 10 might be incorporated in a life size model provided with extremities such as arms and legs filled with mercury to simulate the onset of paralysis by having the extremity become progressively weaker. The entire model could be electrified so that it would be illuminated and correct diagnosis could be made using electrical contacts for various situations and utilizing known plastics which are electrically conductive without the need for wires. Accordingly, in its broad aspect the concepts of this invention might be practiced to provide a dynamic model simulating any particular central nervous system disorder.

What is claimed is:

1. An intracranial pressure monitoring device comprising a pressure sensor, means for mounting said sensor within the skull of a body at the situs where the pressure is to be monitored, pressure indicating means disposed externally of the body, situs pressure transmitting means associated with said sensor for transmitting a value representative of the pressure at the body situs to said indicating means, said body being an inanimate body, said device being in combination therewith, said situs being a simulated body component, pressure creating means mounted externally of said body and connected thereto remote from said simulated component for creating an abnormal pressure condition, and abnormal pressure transmitting means in said body between said pressure creating means and said simulated body component for transmitting the abnormal pressure condition to said simulated body component.

2. The device of claim 1 wherein said abnormal pressure transmitting means is a yieldable mass.

3. The device of claim 2 wherein said pressure creating means includes an inflatable member capable of expanding upon application of pressure therein, a pressure source communicating with said inflatable member, and said yieldable mass being disposed for exerting a pressure against said simulated body component in accordance with the pressure exerted against said mass by said inflatable member.

4. The device of claim 3 wherein said mass is a sponge material simulating the brain.

5. The device of claim 3 wherein said inanimate body includes a simulated skull having a stiff and non-yieldable outer layer to form a housing for said mass, said simulated body component being an elastic sac, and means for conveying a fluid into said sac in accordance with at least one pressure wave characteristic of a corresponding action in the actual counterpart body component which said sac simulates.

6. The device of claim 5 wherein said indicating means is a recorder for producing graphic representations of the pressure at said simulated body component, said sensor being mounted against said simulated body component to sense the pressure therein, and said situs pressure transmitting means being a transducer sending electrical signals from said sensor to said recorder.

7. The device of claim 5 wherein said sac is a simulated ventricle, and said pressure wave corresponding to at least one of a respiratory rate and a pulse rate and a heart rhythm characteristic.

8. The device of claim 5 including a simulated membrane layer disposed against at least a portion of said simulated skull and conforming in shape thereto, and said inflatable member being disposed against said membrane layer on the side thereof opposite said yieldable mass whereby said membrane layer presses against said yieldable mass upon inflation of said inflatable member.

9. The device of claim 8 wherein said conveying means includes a tube communicating with said sac and extending externally of said skull, said tube communicating with a source of fluid whereby fluid may be conveyed into said sac, and pump means connected to said tube to effect a pulsating condition to the fluid supplied to said sac to effect a pressure wave corresponding to at least one of a respiratory rate and pulse rate and heart rhythm characteristic.

10. The device of claim 9 wherein said sac is a simulated first ventricle, a second sac being in said simulated skull simulating the second ventricle, and said tube having a pair of branches each of which communicates with a respective one of said first and said second ventricle.

11. The device of claim 10 wherein at least one of said branches includes valve means for closing fluid communication of its sac with said tube.

12. The device of claim 10 wherein said membrane layer simulates the dura membrane, a second membrane layer being disposed inwardly of the dura membrane to simulate the arachnoid membrane, a second inflatable member being between said dura membrane and said arachnoid membrane, a second pressure source communicating with said second inflatable member, a third membrane disposed inwardly of said arachnoid membrane to simulate the pia membrane, a third inflatable member being between said arachnoid membrane and said pia membrane, and a further inflatable member mounted internally of said pia membrane in said mass.

13. The device of claim 12 wherein said simulated skull is formed in a pair of half-sections representing the front and back of a head, said half-sections being hinged together to provide access to the interior thereof, said front half-section being transparent, and said simulated ventricles being visible through said front half-section.

14. The device of claim 12 wherein a manometer is in flow communication with said tube to provide a visual indication of the pressure.

15. The device of claim 12 wherein said pressure indicating means is a recorder for producing graphic representations of the pressure, said recorder being connected to said tube downstream from said pump to permit said recorder to be responsive to the pressure in said tube, and said tube thereby comprising said situs pressure transmitting means.

16. The device of claim 12 wherein the pressure indicating means is a manometer in flow communication with said tube, said manometer including flexible tube capable of being folded during periods of non-use thereof, said flexible tube having calibrations indicated thereon, and suspending means at the upper end of said flexible tube for permitting said manometer to be suspended in an unfolded condition during use thereof.

* * * * *